(12) United States Patent
Messerschmidt et al.

(10) Patent No.: US 10,932,668 B2
(45) Date of Patent: Mar. 2, 2021

(54) OPTICAL PROBE AND METHOD OF OPERATING THE OPTICAL PROBE

(71) Applicant: GRINTECH GmbH, Jena (DE)

(72) Inventors: Bernhard Messerschmidt, Jena (DE); Gregor Matz, Jena (DE)

(73) Assignee: GRINTECH GmbH, Jena (DE)

( * ) Notice: Subject to any disclaimer, the term of this patent is extended or adjusted under 35 U.S.C. 154(b) by 0 days.

(21) Appl. No.: 16/484,096

(22) PCT Filed: Feb. 28, 2018

(86) PCT No.: PCT/EP2018/054970
§ 371 (c)(1),
(2) Date: Aug. 6, 2019

(87) PCT Pub. No.: WO2018/162303
PCT Pub. Date: Sep. 13, 2018

(65) Prior Publication Data
US 2020/0000341 A1    Jan. 2, 2020

(30) Foreign Application Priority Data

Mar. 6, 2017    (DE) .......................... 102017104617.8

(51) Int. Cl.
*A61B 5/00* (2006.01)
*A61B 1/00* (2006.01)
(Continued)

(52) U.S. Cl.
CPC ........ *A61B 5/0071* (2013.01); *A61B 1/00172* (2013.01); *A61B 1/07* (2013.01);
(Continued)

(58) Field of Classification Search
CPC .................................................. A61B 5/0071
(Continued)

(56) References Cited

U.S. PATENT DOCUMENTS

| 5,901,261 A | 5/1999 | Wach |
| 8,175,423 B2 | 5/2012 | Marple |

(Continued)

FOREIGN PATENT DOCUMENTS

| DE | 102006046554 A1 | 4/2008 |
| DE | 69738291 T2 | 9/2008 |

(Continued)

OTHER PUBLICATIONS

Bergholt, M. et al.: "Simultaneous fingerprint and high-wavenumber fiber-optic Raman spectroscopy enhances real-time in vivo diagnosis of adenomatous polyps during colonoscopy", Journal of Biophotonics 9, No. 4, Apr. 8, 2015, pp. 333-342.

(Continued)

*Primary Examiner* — Tarifur R Chowdhury
*Assistant Examiner* — Omar H Nixon
(74) *Attorney, Agent, or Firm* — Haynes Beffel & Wolfeld LLP; Andrew L. Dunlap (57) ABSTRACT

An optical probe (2) for optically examining an object (1) is described, said optical probe having a first optical beam path for a scanning imaging method and a second optical beam path for a spectroscopic method. The optical probe comprises a first optical fibre (9) in the first optical beam path and a scanning apparatus (10) that is configured to laterally deflect the first optical fibre (9) or illumination light (31) emerging from the first optical fibre (9) for the purposes of scanning the object (1) during the scanning imaging method. The optical probe comprises a second optical fibre (11) in the second optical beam path, said second optical fibre being configured to guide excitation light or detected object light for the spectroscopic method, and a beam splitter filter (15), wherein the beam path of the scanning imaging method and the beam path of the spectroscopic method are brought into partial overlap in the probe (2) by means of the beam splitter (Continued)

filter (15). The optical probe (2) has a diameter of no more than 5 mm. Furthermore, a method for operating the optical probe (2) is specified.

14 Claims, 3 Drawing Sheets

(51) Int. Cl.
- *A61B 1/07* (2006.01)
- *G01J 3/02* (2006.01)
- *G01J 3/44* (2006.01)
- *G02B 3/00* (2006.01)
- *G02B 26/10* (2006.01)
- *G02B 27/14* (2006.01)

(52) U.S. Cl.
CPC .......... *A61B 5/0066* (2013.01); *G01J 3/0218* (2013.01); *G01J 3/4406* (2013.01); *G02B 3/0087* (2013.01); *G02B 26/103* (2013.01); *G02B 26/105* (2013.01); *G02B 27/141* (2013.01); *A61B 1/00165* (2013.01); *A61B 5/0075* (2013.01)

(58) Field of Classification Search
USPC .......................................................... 356/72
See application file for complete search history.

(56) References Cited

U.S. PATENT DOCUMENTS

| | | |
|---|---|---|
| 8,432,542 B2 | 4/2013 | Marple et al. |
| 8,702,321 B2 | 4/2014 | Marple et al. |
| 2007/0046778 A1* | 3/2007 | Ishihara ............. G01N 21/6456 348/68 |
| 2008/0058629 A1 | 3/2008 | Seibel et al. |
| 2011/0282166 A1 | 11/2011 | Chen et al. |
| 2015/0049339 A1 | 2/2015 | Tearney et al. |
| 2015/0366437 A1* | 12/2015 | Labrie ................. A61B 5/0084 600/373 |
| 2016/0000312 A1 | 1/2016 | Seibel et al. |
| 2016/0235278 A1 | 8/2016 | Goebel et al. |

FOREIGN PATENT DOCUMENTS

| | | |
|---|---|---|
| DE | 102006046555 B4 | 12/2010 |
| JP | 2004/065965 A | 3/2004 |
| WO | 2000/032102 A1 | 6/2000 |
| WO | 2010/086861 A1 | 8/2010 |

OTHER PUBLICATIONS

Day, J. C. et al.: "A miniature confocal Raman probe for endoscopic use" Phys. Med. Biol. 54, Nov. 11, 2009, pp. 7077-7087.

Hollricher, O.: "Confocal Raman microscopy teams high-resolution capabilities with powerful materials analysis.", Spie's OE Magazine, Nov. 2003, pp. 16-20.

Huang, Z. et al.: "Integrated Raman spectroscopy and trimodal wide-field imaging techniques for real-time in vivo tissue Raman measurements at endoscopy.", Optics Letters, vol. 34, No. 6, Mar. 15, 2009, pp. 758-760.

Jeong, S. et al.: "Fluorescence-Raman Dual Modal Endoscopic System for Multiplexed Molecular Diagnostics.", Scientific Reports 5, Mar. 30, 2015, pp. 1-9.

Patil, C. A. et al.: "Clinical Instrument for Combined Raman Spectroscopy—Optical Coherence Tomography of Skin Cancers" Lasers Surg Med., vol. 43, Issue 2, Feb. 2011, pp. 143-151.

Blattmann, M. "Bimodal endoscopic prove combing white-light microscopy and optical coherence tomogrpahy", Applied Optisc, vol. 55, No. 15, May 2016, pp. 4261-4269.

Mavadia, J, "An all-fiber-otic endoscopy platform for simultaneous OCT and fluoresence imaging", Biomedical Optics Express , vol. 3 No. 11, 9 pgs.

PCT/EP2018/054970—International Search Report and Written Opinion dated Sep. 13, 2018, 14 pages.

* cited by examiner

OPTICAL PROBE AND METHOD OF OPERATING THE OPTICAL PROBE

CROSS-REFERENCE

This application is the U.S. National Stage of International Application No. PCT/EP2018/054970, filed 28 Feb. 2018, which claims priority to German Patent Application No. DE 102017104617.8, filed 6 Mar. 2017.

DESCRIPTION

The invention concerns an optical probe, in particular a miniaturized imaging optical probe, which is suitable, for example, for the examination of tissue in biology or medicine.

Miniaturized imaging probes, which can be introduced to an object to be examined, are of particular interest in biological research or in medicine in order to enable minimally invasive examinations or to observe living tissue under normal living conditions over longer periods of time.

Optical coherence tomography (OCT) has particular potential for the 3-dimensional imaging of the morphology of tissue layers several millimeters thick, for example, and Raman spectroscopy for the identification of molecular chemical components of tissue, Multiphoton fluorescence microscopy for high-resolution submicron differentiation of chemical tissue components (especially endogenous fluorophores such as NADPH and flavins as well as exogenous chromophores), frequency doubling (SHG, second harmonic generation) to locate regularly arranged cell components such as collagen, microtubules and myosin, microscopy based on coherent Anti-Stokes Raman scattering (CARS, Coherent Anti-Stokes Raman Scattering) or Microscopy based on stimulated Raman scattering (SRS) for molecular-chemically differentiating imaging.

The invention is based, in at least one aspect, on the task of indicating a miniaturized optical probe and a method for operating the optical probe, the probe enabling biological or medical investigations with further improved sensitivity.

According to at least one configuration, the optical probe comprises a rear end for connection to a control unit and a front end for optical examination of an object. In particular, the front end of the probe is provided with a light transmission opening through which illuminating light from the probe can be directed towards an object such as tissue in biological or medical examinations. In addition, object light returning from the object through the light transmission opening, which is produced by the interaction of the illumination light with the object, can enter the probe again. At the rear end, the probe can be connected optically and electronically to a control unit via a connecting cable, which is used in particular for controlling the probe and for signal evaluation.

The probe advantageously contains a first optical beam path for a scanning imaging method and a second optical beam path for a spectroscopic method. The probe is intended in particular for examining an object using two different optical methods, at least one of the methods being an imaging method in which a two- or three-dimensional region of the object is optically scanned by a scanning method. The second method is advantageously a spectroscopic method, preferably confocal Raman spectroscopy. The optical probe is thus a multimodal probe, whereby two optical beam paths in the probe make it advantageously possible to examine an object using an imaging method and a spectroscopic method. In particular, it may be possible to alternately examine an object with the imaging method and with the spectroscopic method at an object location to be examined. In this way, the sensitivity and specificity of an examination procedure that can be performed with the probe is advantageously increased.

In particular, the optical probe enables the combination of an imaging method such as OCT, multiphoton microscopy, confocal single photon fluorescence- or reflection microscopy or CARS/SRS microscopy, in which the object plane is scanned in a point-focused manner by a suitable excitation or illumination light, with a confocal arrangement of Raman excitation and detection of the inelastically scattered spectrum. Since the Raman signal shifted into the long wavelength is very weak and can amount to only about $10^{-12}$-th of the excitation intensity, a spatially resolved Raman imaging is not useful for medical and biological applications on living tissues or organs, so that a Raman signal is preferably only recorded selectively or integrally over a limited excitation spot, preferably in the center of the image field of the imaging probe.

According to at least one embodiment, the probe comprises a first optical fiber in the first optical beam path configured to direct an illumination light for the scanning imaging method towards the front end of the probe and to direct object light returning from the object to the rear end of the probe. The illumination light can in particular be generated by a light source in the control unit of the probe, guided to the probe by means of a fiber connection and coupled into the first optical fiber at the rear end of the probe, for example by means of a fiber coupling. In the opposite direction, the object light can be guided to the control unit for evaluation.

Further, the probe advantageously comprises a scanning device configured to laterally deflect the first optical fiber or illumination light exiting the first optical fiber for scanning the object in the scanning imaging method. The scanning device is advantageously a movable electronically controllable element, in particular a fiber scanner or a mirror scanner. In the case of the fiber scanner, the beam deflection takes place before the illumination light leaves the first optical fiber by deflection of the fiber. In the case of the mirror scanner, the beam deflection takes place after the illumination light emerges from the first optical fiber by the deflection of a mirror on which the illumination light is incident. In particular, the scanning device enables two-dimensional lateral beam deflection in order to scan the object in a two-dimensional raster during the imaging method. In this way, a beam guidance and an active, electronically controllable beam deflection for the imaging method are realized in the first beam path.

According to at least one configuration, the second beam path in the probe has a second optical fiber. The second optical fiber is advantageously configured to guide an excitation light or a detected object light for the spectroscopic method. The second optical fiber is preferably arranged parallel to the first optical fiber in the probe. The second optical fiber preferably has a core diameter of 3 µm to 300 µm and a numerical aperture of 0.08 to 0.3. The excitation light for the spectroscopic method can in particular be generated by a light source in the control unit of the probe, guided to the probe by means of a fiber connection and coupled into the second optical fiber at the rear end of the probe, for example by means of a fiber coupling. In the opposite direction, the object light can be guided to the control unit for evaluation.

According to at least one configuration, the probe has a beam splitter filter. In particular, the beam splitter filter can be set up to merge the first beam path and the second beam path within the probe, at least in certain areas. In particular, the beam splitter filter at least partially combines the beam path of the scanning imaging method and the spectroscopic method. The at least partial combination of the beam paths is advantageous in order to be able to guide the beam paths for both methods in the miniaturized probe with a diameter of in particular not more than 5 mm. In particular, the combination of the beam paths enables the simultaneous use of at least part of an optical lens arrangement in both beam paths. The beam splitter filter is preferably designed as a beam splitter plate or as a prism beam splitter cube. The beam splitter filter, for example a beam splitter cube, is advantageously wavelength-selective, in particular colour splitting.

According to at least one embodiment, the second optical fiber is configured to guide the excitation light of the spectroscopic method and the first optical fiber is configured to guide the detected light of the spectroscopic method. Alternatively, the first optical fiber is configured to guide the excitation light of the spectroscopic method and the second optical fiber is configured to guide the detected light of the spectroscopic method. In both cases, the excitation light and the detected light of the spectroscopic method are advantageously not guided in the same optical fiber. In this way, it is advantageously avoided that an interfering signal, which could be caused by the excitation light of the spectroscopic method in the first or second optical fiber, is superimposed on the detected light and led to the evaluation unit.

According to at least one configuration, the beam splitter filter is wavelength-selective. In particular, the beam splitter filter is configured to separate the excitation light and the detected light of the spectroscopic method. The detected light of the spectroscopic method, i.e. the light coming from the object, has in particular longer wavelengths than the excitation light. The reflection and transmission of the beam splitter filter are preferably adjusted in such a way that the excitation light of the spectroscopic method is essentially transmitted and not reflected, or vice versa, the excitation light of the spectroscopic method is essentially reflected and not transmitted. For example, the excitation light of the spectroscopic method can be reflected by the beam splitter filter and the detected light can be transmitted. Alternatively, the excitation light of the spectroscopic method can be transmitted by the beam splitter filter and the detected light reflected.

According to at least one configuration, the beam splitter filter is transmitting for the illumination light and for the object light returning from the object of the scanning imaging method. In contrast to the spectroscopic method, the beam splitter filter for the imaging method transmits in both directions. In particular, both the illumination light and the object light of the imaging method are guided in the first optical fiber.

The first optical beam path and the second optical beam path overlap in the probe advantageously at least partially. In particular, the first optical beam path and the second optical beam path can overlap at the front end of the probe, whereby at least one lens element can be arranged simultaneously in the first optical beam path and the second optical beam path. This allows a compact design of the optical probe with few optical components.

According to at least one configuration, the optical probe has a diameter of no more than 5 mm, in particular in the range between 1 mm and 5 mm. The probe is therefore a miniaturized optical probe. In particular, the optical probe can be an endoscopic probe. Due to the miniaturization, the probe advantageously enables the examination of the object with at least one imaging method and at least one spectroscopic method in a minimally invasive way, in particular by means of endoscopy.

According to at least one configuration, the probe comprises at least one lens element for beam shaping the illumination light and/or the object light, wherein the at least one lens element is arranged at least regionally between the first optical fiber and the front end of the probe.

In a configuration of the optical probe, the scanning device is a fiber scanner which acts in particular on the first optical fiber in the first optical beam path. The fiber scanner is preferably configured to cause a radial deflection of the first optical fiber of no more than ±1.2 mm.

In particular, the fiber scanner can be a piezoelectric fiber scanner. The fiber scanner is advantageously electrically controllable by a control unit of the probe.

In an alternative configuration of the optical probe, the scanning device is a mirror scanner. The mirror scanner preferably comprises a mirror with a diameter of not more than 2 mm. Preferably, the mirror scanner is configured to cause a beam deflection of not more than ±20°. The mirror scanner is advantageously electrically controllable by a control unit of the probe. In particular, the mirror scanner can be a MEMS micro-mirror scanner.

According to at least one configuration, the first optical fiber has an inner fiber core and an outer fiber core. The inner fiber core should preferably be dimensioned in such a way that it forms a single mode fiber at the excitation wavelength of the method. The outer fiber core preferably has a core diameter between 20 µm and 300 µm and a numerical aperture between 0.15 and 0.4.

According to at least one configuration, the optical probe comprises at least one lens element having a gradient index lens or consisting of a gradient index lens. A gradient index lens has a refractive index profile that can be advantageously adjusted to correct optical aberrations. The gradient index lens allows such a correction of optical aberrations with a small size compared to complex conventional lens systems. The use of at least one gradient index lens is therefore advantageous in order to achieve a particularly compact design of the optical probe.

According to at least one configuration, the second beam path contains at least one optical filter for the selection of a wavelength range for the spectroscopic method. The spectroscopic method is preferably Raman spectroscopy. In Raman spectroscopy, the excitation light and the detected light can overlap in the object space. In particular, the spectroscopic method can be confocal Raman spectroscopy.

In a method for operating the optical probe, an object, in particular an object to be examined in the field of biology or medicine, is examined by means of the optical probe using at least one scanning imaging method and at least one spectroscopic method.

The scanning imaging method is advantageous one of the following methods: optical coherence tomography (OCT), CARS microscopy, SRS microscopy, multiphoton microscopy, SHG multiphoton microscopy, confocal single photon fluorescence, reflection microscopy. Furthermore, the spectroscopic method is preferably confocal Raman spectroscopy. The mentioned methods differ in their specificity and sensitivity. For applications in medicine and biology, the synergy of at least two such methods is therefore of particular advantage.

Further advantageous configurations of the method for operating the optical probe can be found in the description of the optical probe and vice versa.

In the following, the invention will be explained in more detail using examples in connection with FIGS. 1 to 9.

BRIEF DESCRIPTION OF THE FIGURES

The included drawings are for illustrative purposes and serve only to provide examples of possible structures and process operations for one or more implementations of this disclosure. These drawings in no way limit any changes in form and detail that may be made by one skilled in the art without departing from the spirit and scope of this disclosure. A more complete understanding of the subject matter may be derived by referring to the detailed description and claims when considered in conjunction with the following figures, wherein like reference numbers refer to similar elements throughout the figures.

DETAILED DESCRIPTION

Same or similarly acting components are provided in the figures with the same reference signs. The represented components as well as the proportions of the components among each other are not to be regarded as true to scale.

Figure 1:
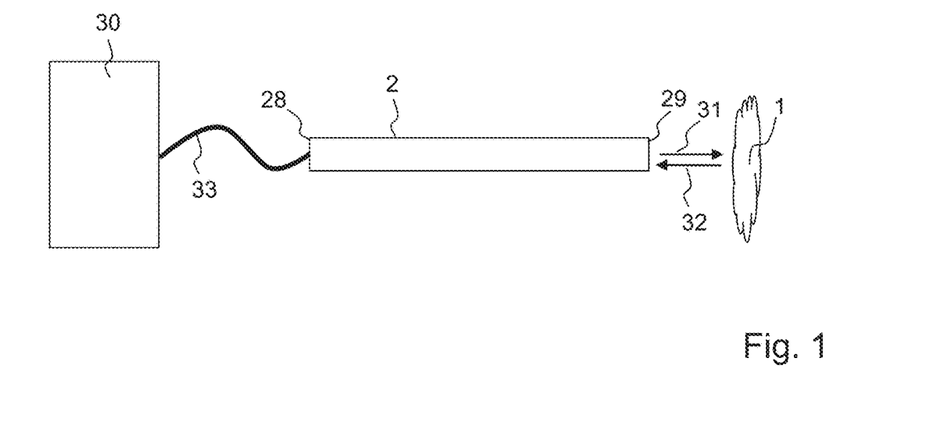
FIG. 1 shows a schematic representation of an optical arrangement for examining an object by means of an optical probe according to an example, and FIGS. 2, 3, 4, 5, 6, 7, 8 and 9 each show a schematic representation of a cross-section through an optical probe according to an example.

FIG. 1 schematically shows an optical arrangement for examining an object 1 using an optical probe 2. The optical probe 2 is a miniaturized imaging probe which is advantageously suited for endoscopic use. The optical probe has a diameter of no more than 5 mm, preferably in the range from 1 mm to 5 mm. The object 1 can in particular be human or animal tissue.

The optical probe 2 has a rear end 28 and a front end 29. The front end 29 of the probe faces the object 1 to be examined when the probe 2 is in operation. At the front end 28, illumination light 31 can be decoupled from probe 2 and directed at the object 1, and object light 32 coming back from the object 1 can be coupled into the optical probe. An object field diameter of the probe 2 is preferably about 0.2 mm to 3 mm, for example 0.2 mm to 1 mm with a numerical aperture (NA) of 0.8 to 0.15 and about 1 mm to 3 mm with an NA of 0.15 to 0.05.

The rear end 28 can preferably be connected to a control unit 30 by means of a connecting cable 33, which may comprise one or more optical fibers and electrical connecting cables. The control unit 30 is used in particular to control the probe 2 and for signal evaluation.

By means of the connecting cable 33, illumination light 31 can be led from the control unit 30 to the probe and object light 32 from the probe 2 to the control unit 30. The control unit 30 can in particular have one or more light sources for operating the optical probe 2, which are advantageously connected to the probe 2 by means of optical fibers in the connecting cable 33.

The control unit 30 can also have components for the optical, in particular spectroscopic analysis of the object light 32 received by the probe. The control unit 30 may also have components for electronic image processing and display or be connected to suitable equipment.

The optical probe 2 is advantageously suited for the examination of the object 1, in particular tissue, with at least two different optical methods. Suitable configurations of the optical probe 2 for this purpose are described in connection with the following examples.

Figure 2:
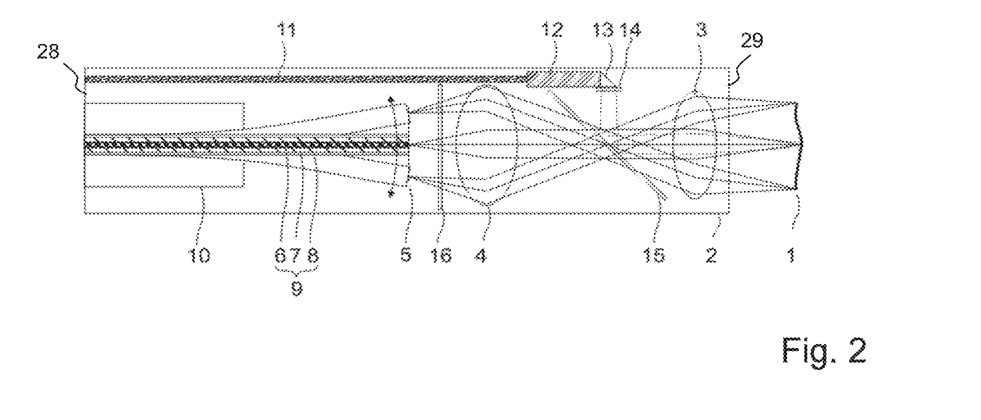

FIG. 2 shows a first example of the optical probe 2, which is suitable for examining an object 1, in particular tissue, using at least two optical methods. One method is advantageously a quasi-confocal imaging method in which illumination light is guided in a first optical fiber 9 to the front end of the optical probe 2. The illumination light emerging from an inner fiber core 6 of the first optical fiber 9 passes through a first filter 16 which is spectrally transparent for the illumination wavelength, is bundled with a first lens element 4, passes through a further inclined beam splitter filter 15 which is spectrally transparent for the illumination wavelength and is focused with a further lens element 3 on the object 1 to be examined. The first lens element 3 and the second lens element 4 can each comprise a lens or a lens group.

The illumination light is absorbed, scattered or reflected depending on the nature of the object 1, in particular the tissue morphology or composition. The object light emanating from object 1 is collected, transmitted and confocally imaged or coupled into the first optical fiber 9 by the optical arrangement comprising lens elements 3, 4 and filters 15, 16. The first optical fiber 9 has a second outer fiber core 7 concentrically arranged around the inner fiber core 6, the second outer fiber core 7 being protected by a cladding 8. Light from object 1 can be coupled into both the inner fiber core 6, through which the illumination light is guided, and the larger outer fiber core 7. This is due to the fact that total confocality is usually not complete, because the light from the object is also backscattered from deeper or flatter tissue layers, or in the case of fluorescence in the object can also be spectrally shifted to the illumination light.

At the rear end 28 of probe 2, a separate coupling of the light into and out of the inner fiber core 6 and outer fiber core 7 can be performed by suitable fiber couplers (not shown). The inner fiber core 6 can function as a single-mode fiber, for example in the wavelength range from about 800 nm to 1600 nm if the probe 2 is intended for optical coherence tomography (OCT), or in the wavelength range between 400 and 1500 nm if the probe is intended for multiphoton, CARS, fluorescence or SRS microscopy. The outer fiber core 7 functions in particular as a multimode fiber and has, for example, a core diameter between 20 and 300 µm and a numerical aperture between 0.15 and 0.4.

In the example shown in FIG. 2, the imaging is based on the fact that the first optical fiber 9 can be deflected laterally by a fiber scanner 10. The fiber scanner 10 allows advantageously a radial deflection of the fiber tip of preferably about 1 mm in diameter, for example up to about 1.2 mm. By laterally deflecting the fiber tip through the fiber scanner 10 in the intermediate image area 5, the object 1 is scanned in a focused manner.

Particular implementations and examples—are provided below.

Excitation and detection at the same wavelength, whereby the object light backscattered into the inner fiber core 6 is used for imaging. In the case of optical coherence tomography, the optical path from the exit of the first optical fiber 9 to the object 1 and back into the first optical fiber 9 is externally determined by an interferometric evaluation, so that a 3D reconstruction of the structure of the object 1 is possible.

Excitation of a single photon fluorescence in the object 1 to be investigated by the illumination wavelength. The long-wave shifted light emitted from object 1 passes the lens element 3, the filter 15, the lens element 4 and the filter 16 and is coupled into the outer fiber core 7 and detected as a function of the fiber deflection. The outer fiber core 7, which typically has a larger core cross-section and a higher numerical aperture than the inner fiber core 6, serves as a confocal diaphragm. Confocality can be specifically influenced by suitable matching of core diameter and NA.

Excitation of two- or three-photon fluorescence or generation of the second harmonic (SHG) in the object 1 to be investigated by the illumination wavelength. This is a non-linear absorption process at high excitation powers or intensities. The SHG light or fluorescent light to be detected is produced at or above half the wavelength (2-photon fluorescence) or a third of the excitation wavelength, but well below the excitation wavelength itself. Also in these wavelength ranges the filters 15, 16 are advantageously transmissive. The light emitted by object 1 from the surrounding area of the excitation spot is guided via lens elements 3, 4 and filters 15, 16 to the scanning first optical fiber 9 in a quasi-confocal manner and coupled into the outer fiber core 7. The outer fiber core 7 thus forms a confocal diaphragm, which is determined by the diameter of the outer fiber core 7 and its numerical aperture (NA). Depending on how large the outer fiber core 7 and the NA are selected, confocality can be attenuated and collection efficiency increased. In this case, confocality results from the fact that the SHG, 2- or 3-photon fluorescent light is produced only in the focus volume of the excitation spot, where the excitation intensity is correspondingly high, due to the non-linearity of the excitation process.

Excitation of a coherent anti-Stokes Raman scattering signal (CARS) or a stimulated Raman scattering signal in the object. This is a non-linear optical process in which mutually coherent laser pulses of different wavelengths are conducted in the inner fiber core 6 in the direction of the front end 29 of the probe 2 and are focused on the object 1 via the filters 16, 15 transmitting at these wavelengths and the lens elements 4, 3. In both cases, certain molecular oscillations are excited in the object 1, whose emitted optical radiation at shorter wavelengths represents a quantitative signal of the concentration of the molecule in the object 1. In the case of CARS, the object light is coupled into the outer fiber core 7 through the lens elements 3, 4 and through the filters 15, 16 transparent at these CARS wavelengths, so that it can be detected for imaging as a function of the fiber deflection and thus the lateral object plane position. The lens elements 3, 4 and filters 15, 16 are advantageously used for the imaging methods described to achieve a high imaging quality of the optical arrangement.

With the optical probe 2, the scanning imaging method is advantageously coupled with a second Raman spectroscopic modality in a highly miniaturized manner. Since the Raman signal is very weak, high-resolution imaging with long integration times therefore does not appear to be useful for clinical or in vivo investigations, and a highly effective spectral separation between the excitation and Raman signals is necessary, it is advantageous for optical probe 2 to have point confocal Raman excitation and detection in the center of the image field.

In a first configuration, the Raman excitation light, typically a laser light at a particularly stabilized wavelength (e.g. 785 nm), is guided to the front end 29 of the probe via a second optical fiber 11 arranged parallel to the first optical fiber 9. The second optical fiber 11 preferably has a core diameter of about 3-300 µm. The NA of the second optical fiber 11 is preferably about 0.08 to 0.4. The Raman excitation light is preferably adjusted in its divergence via a beam shaping element 12 and guided via a deflecting element 13 onto the inclined beam splitter filter 15. A spectral filter 14 attached to the beam shaping element 12 or to the deflecting element 13 allows only the narrow-band Raman excitation light to pass through and particularly filters out the intrinsic Raman background induced in the second optical fiber 11 (so-called laser cleaning filter), which would lie in the spectral range finally emitted by the object 1 as a Raman signal. The beam splitter filter 15 is advantageously highly reflective for the wavelength of the Raman excitation, so that the light is directed to the object 1. The deflection element 13 and the beam splitter filter 15 are arranged so that the Raman excitation light forms an illumination spot on the object 1 which is almost concentric to the optical axis (on-axis) of the scanning system (dotted line in FIG. 2).

The Raman light, which is generated in a spot volume illuminated by the Raman excitation and spectrally shifted to larger wavelengths with respect to the Raman excitation, is collected and bundled to the largest possible extent by the lens element 3. The spectral filters 15 and 16 are designed to transmit the Raman detection light as efficiently as possible. The lens element 4 focuses the bundled Raman signal on the inner and outer fiber cores 6, 7 of the first optical fiber 9. The first optical fiber 9 directs the Raman signal to the rear end of probe 2, where it can be coupled via a suitable fiber coupler or switch into a spectrometer that analyzes the Raman spectrum. The filter 16 has a reverse function to the filter 14. It blocks the spectral part of the Raman excitation so that the Raman spectrum to be detected is not superimposed by a strong excitation peak. Due to the confocality of the excitation and detection, the Raman signal will be largest when the first optical fiber 9 is not deflected by the fiber scanner 10 but is located on the optical axis. However, mounting tolerances of the optical system may be compensated by a defined static or dynamic deflection of the first optical fiber 9 by the fiber scanner 10.

Example 1

Raman excitation takes place at a wavelength of about 785 nm. In this case the spectral filter 14 serves as a bandpass from 780 to 790 nm or as a low pass for wavelengths below 790 nm and has a strong blocking effect between 800 and 1000 nm. The filters 15, 16 preferably have a high reflection from 780 nm to 790 nm and a high transmission in the spectral range from 400 nm to 775 nm and from 800 nm to 1400 nm. Thus, the Raman spectrum of the object 1 between 800 nm and 1000 nm is directed onto the first optical fiber 9.

In the case of single photon fluorescence imaging, excitation light in the range from 400 nm to 550 nm from the inner fiber core 6 can be focused on the object 1. The fluorescence light above the excitation wavelength but below 775 nm is detected by the inner and outer fiber cores 6, 7 and can be separated from the excitation light by color splitters. In the case of OCT imaging, light in the range 800 nm-1400 nm can be directed from the inner fiber core 6 to the object 1 and the backscattered or reflected light of the object 1 can be received by the inner fiber core 6.

In the case of multiphoton microscopy imaging, excitation light in the range below 780 nm or above 800 nm is focused from the inner fiber core 6 onto the object 1. The SHG or multiphoton fluorescence light between 400 and 775 nm is received by the outer fiber core 7. In the case of CARS or SRS imaging, light from pump and Stokes excitation in the spectral range between 800 nm and 1400 nm is directed from the fiber core 6 onto the object. The CARS signal below 775 nm can be efficiently received by the outer fiber core 7.

In an alternative second configuration, Raman excitation can also be performed through the inner fiber core 6, where filters 15, 16 transmit both the Raman excitation and the wavelengths of the imaging method, but have a strong blocking effect in the spectral region above the Raman excitation wavelength where Raman spectra are to be detected. This blocking effect is advantageous to filter out fiber intrinsic self-fluorescence in this spectral range and not to focus on object 1. The inclined beam splitter filter 15 has a high reflection in the range of the Raman spectrum to be detected. The punctiform or spot-shaped detection of the Raman light from the object 1 is in this case carried out by the fiber-optic Raman detection unit arranged confocally to the first optical fiber 9, comprising the filter 14, which has a high transmission in the Raman detection range, but a strong blocking effect in the Raman excitation range, the deflection unit 13, the beam-forming element 12 and the second optical fiber 11, which functions as a Raman collection fiber.

Example 2

In an example, Raman excitation takes place at a wavelength of about 785 nm. The filters 15, 16 have a high transmission between 400 nm and 795 nm, a very strong blocking effect between 800 nm and 1000 nm and a high transmission between 1000 nm and 1300 nm. The beam splitter filter 15 has a high reflection in the range between 800 nm and 1000 nm. This allows the Raman spectrum of the object 1 between about 800 nm and 1000 nm to be guided in the direction of the rear end 28 of the probe 2 by means of the deflection element 13 and the second optical fiber 11, in particular for detection in a connected evaluation unit. In the case of single-photon fluorescence imaging, excitation light in the wavelength range from 400 nm to 550 nm, for example, can be focused from the inner fiber core 6 onto object 1. The fluorescence light above the excitation wavelength but below 795 nm can be received by the inner and outer fiber cores 6, 7 and separated from the excitation light by color splitters. In the case of OCT imaging, light in the range 1000 nm-1400 nm can be directed from the inner fiber core 6 to the object 1 and the backscattered or reflected light of the object 1 can also be received from the inner fiber core 6. In these cases, the first optical fiber 9 can also be in the form of a single-core fiber (with one fiber core 6). In the case of multiphoton microscopy imaging, excitation light in the range below 780 nm or in particular in the case of 3-photon fluorescence above 1000 nm can be focused from the inner fiber core 6 onto object 1. The multiphoton fluorescence light between 400 nm and 795 nm can be collected by the outer fiber core 7. In the case of CARS or SRS imaging, light from pump and Stokes excitation in the spectral range below 795 nm and between 1000 nm and 1400 nm can be directed from the inner fiber core 6 to object 1. The CARS signal below 795 nm can be received by the outer fiber core 7.

Figure 3:
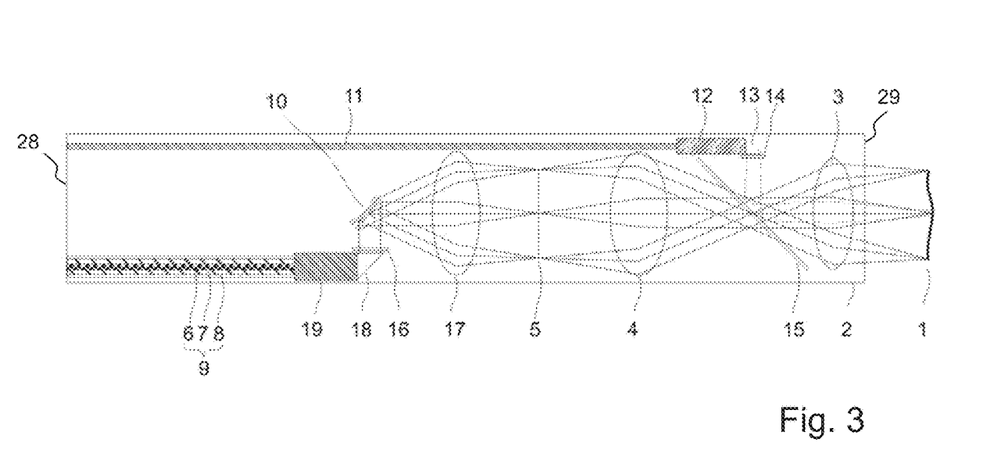

FIG. 3 shows another example of the optical probe 2 according to a third embodiment. In this configuration, the imaging is based on a mirror scanner 10. The illumination light for the imaging is guided in the inner fiber core 6 of the first optical fiber 9 arranged parallel to the axis of the probe 2 to the front end 29 of the probe 2. The illumination light emerging from the first optical fiber 9 is advantageously collimated, focused or reduced in its divergence by a beam-forming optical element 19. A deflection element 18 directs the illumination light to the mirror scanner 10. This mirror scanner 10 deflects the illumination light by reflection at an angle with respect to the optical axis of the probe 2. An optical element 17 following the mirror scanner 10 generates an intermediate image plane 5 from these deflected, collimated or slightly divergent bundles. This intermediate image plane 5 thus replaces the fiber scan plane of the embodiments according to FIG. 2. The focal lengths, positions and deflection angles of the optical components 10, 17, 18, 19 are selected in such a way that for all scan angles that span the image field of the entire probe 2, a minimum shading and vignetting results in the area between the first optical fiber 9 and the object 1. The multimodal imaging and Raman detection is otherwise analogous to the first two embodiments. The filter 16 can be arranged in the spaces between the deflection element 18 and the lens element optics 4. However, a particularly favorable position is on the exit surface of the deflector element 18 or in the space between the deflector element 18 and the mirror scanner 10, since the bundle is very narrowly limited here and has small divergence angles.

A high imaging quality of the optical probe 2 is required for all imaging methods described, so that on the one hand a high resolution is achieved, but on the other hand also high photon yields or collection efficiencies are achieved in confocal imaging. The optical probe 2 is preferably designed in such a way that it scans as large an object field as possible with as high a numerical aperture as possible while maintaining maximum compactness of the system, thus maximizing the etendue. In addition, the spherical aberration and off-axis imaging errors, such as coma and astigmatism, are advantageously corrected so well that the light emerging from the inner fiber core acting as a single-mode excitation fiber can be focused almost diffraction-limited within the entire object field and no or hardly any vignetting losses occur. Due to the confocality of the arrangement for all modalities, it is also necessary to correct the longitudinal and transverse chromatic aberrations for the respective wavelengths involved. For the combinations with a Raman spectroscopy method described below, this concerns the correction for the following wavelengths:

(i) OCT or reflection and scattered-light imaging: OCT wavelength range (typically 1200 nm-1400 nm) or visible spectral range between 440 and 650 nm, as well as Raman detection or excitation (depending on configuration)

(ii) Single photon fluorescence: fluorescence excitation and detection (typically 400 nm-700 nm) as well as Raman detection and excitation (depending on the configuration)

(iii) Two- and three-photon fluorescence: excitation (typically between 750 nm and 1300 nm), fluorescence (typically between 400 and 600 nm), and Raman detection or excitation (depending on configuration)

(iv) CARS and SRS microscopy: very good correction for Pump and Stokes wavelengths (typically 750 nm-850 nm and 1000 to 1200 nm), as there must be a very good overlap between the excitation focal lengths for both wavelengths in the object plane, for CARS detection (typically between 550 and 750 nm), and for Raman detection or excitation (depending on the configuration).

Figure 4:
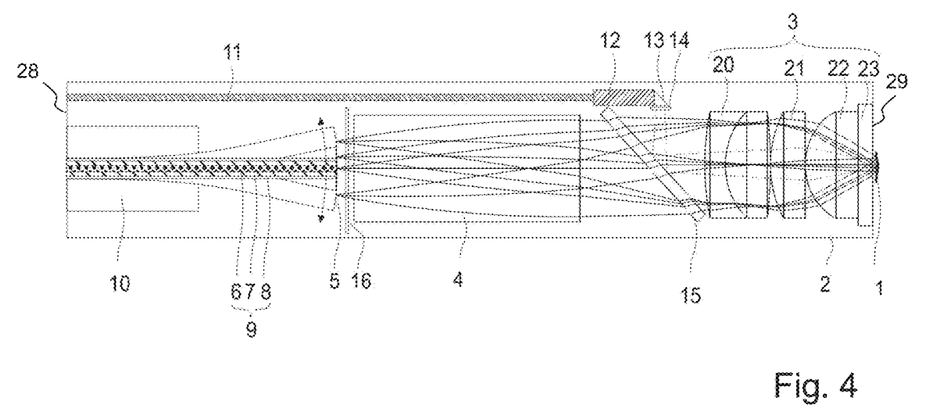

This correction can be achieved in embodiments of the optical probe 2 having a fiber scanner 10 (as shown in FIG. 2) especially as described below. FIG. 4 shows an example of the optical probe in which the lens element 4 is a gradient index (GRIN) lens with a radial refractive index profile and vertical end faces. The beam splitter filter 15 is preferably designed as a thin plate, which leads to a slight beam offset in the transmission direction, or as a prism beam splitter cube. In the example, the front lens element 3 is composed of a spherical doublet lens 20, a plano-convex lens 21, a further plano-convex lens 22 and an optional front window 23, which advantageously has a scratch-resistant surface and hermetically seals the probe 2. The color correction is achieved by a coordinated selection of the refractive lens glasses with the GRIN lens 4. The refractive index profile of the GRIN lens 4 is adjusted in such a way that the spherical aberration, astigmatism and coma of the entire system are corrected in such a way that an almost diffraction-limited image quality results. This design is particularly advantageous if a high numerical aperture in the range of 0.45 to 1.0 is to be achieved in the object space, e.g. for confocal single-photon fluorescence microscopy, multiphoton microscopy or CARS or SRS microscopy.

Figure 5:
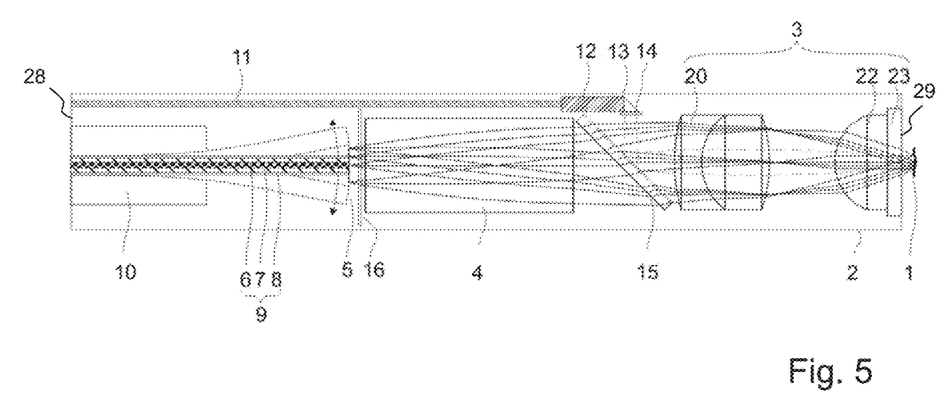

FIG. 5 shows a further example of the optical probe 2 where, in contrast to FIG. 4, the plano-convex lens 21 is not present in the front lens element 3. The plano-convex lens 21 can be advantageously omitted, in particular, if the numerical aperture is approx. 0.45 to 0.6.

Figure 6:
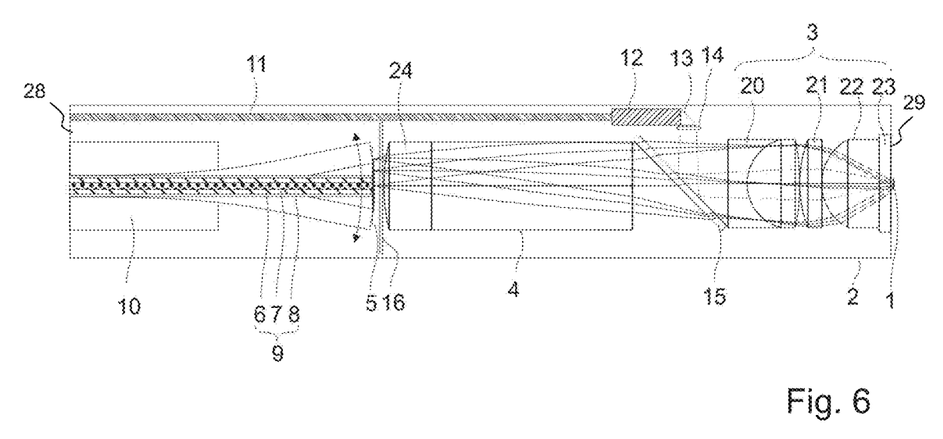

In a specific configuration shown in FIG. 6, in which the NA of the inner fiber core 6 of the first optical fiber 9, for example, is greater than 0.18 and the lateral deflection of the tip of the first optical fiber 9, for example, is more than 60% of the lens radius of the GRIN lens 4, a further plano-convex lens 24 is advantageously placed on the rear of the GRIN lens 4. In this way it is possible to greatly reduce vignetting and obtain a well corrected system overall.

Figure 7:
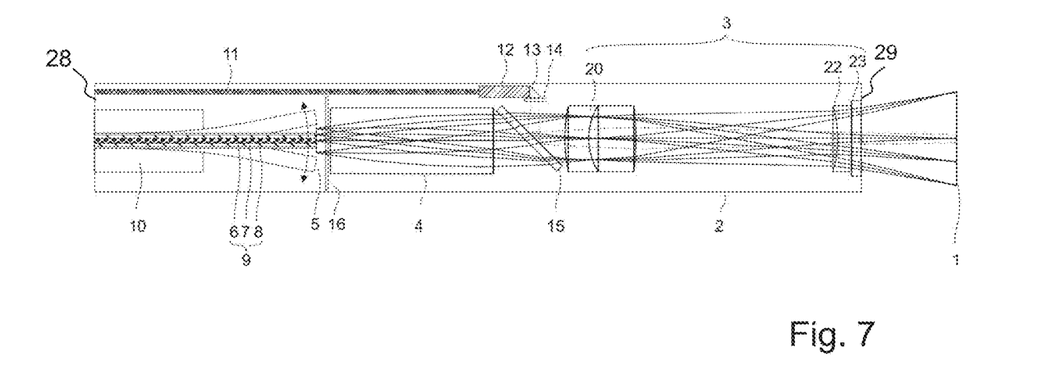

FIG. 7 shows another example of the optical probe 2. In the case of OCT and classical endoscopic imaging, larger object fields can be scanned with a low numerical aperture. It has proved to be particularly advantageous to use an arrangement according to FIG. 7 for the configuration with the fiber scanner 10. The lens element 4 of this arrangement is preferably a GRIN lens with a radial refractive index profile and flat vertical end faces. The front lens element 3 preferably consists of a doublet lens 20, a plano-concave lens 22 and an optional front window 23, which in particular guarantees the scratch resistance and tightness of the probe 2. A plano-concave lens 22 is advantageously used to achieve a large image field with low NA. Due to the comparatively low object NA and a large image field, the plano-convex lens 21 used in some previous examples can be dispensed with in this example. A good color correction can be achieved by a coordinated selection of the refractive lens glasses with the GRIN lens 4. The refractive index profile of the GRIN lens 4 is adjusted in such a way that the spherical aberration, astigmatism and coma of the entire system are corrected in such a way that the image quality is almost diffraction-limited. This design is particularly advantageous if a low numerical aperture of less than 0.1 is to be achieved in the object space, e.g. for OCT or endoscopic imaging with a large depth of field.

Figure 8:
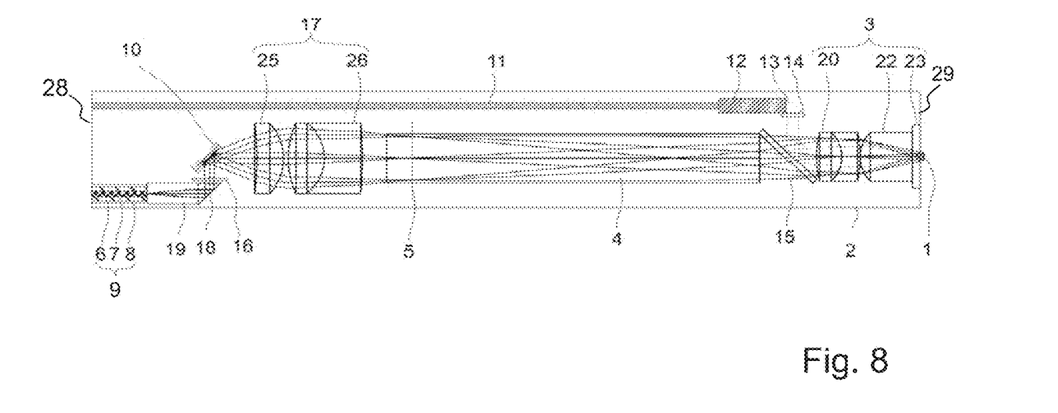

FIG. 8 shows another example of the optical probe in which the image is generated by a miniaturized mirror scanner 10. In this example, the optical element 17 following the mirror scanner 10 is advantageously realized by a system of two refractive spherical lenses, in particular a meniscus lens 25 and a doublet lens 26. These generate an intermediate image plane 5 from the collimated or only slightly divergent bundle, which meets the mirror scanner 10 after the beam-forming optical element 19 and the deflecting element 18. The components are matched in such a way that this intermediate image plane 5 is corrected almost diffraction-limited with regard to spherical aberrations, astigmatism, coma and chromatic aberrations for the entire usable image field, which is spanned by the mirror scanner 10. In addition, the optical element 17 ensures an almost telecentric guidance of the illumination light in the intermediate image plane 5, which minimizes vignetting of the illumination light in the further course of the beam path via the lens element 4, the beam splitter filter 15 and the front lens element 3. This achieves a uniform brightness in the area of the object 1.

For microscopic imaging with a high numerical aperture and the associated high resolution in the object plane, the first lens element 4 is preferably a GRIN lens, the beam splitter filter 15 a beam splitter plate and the front lens element 3 a lens arrangement comprising a doublet lens 20, a plano-convex lens 21, a further plano-convex lens 22 and an optional front window 23. The entire optical system is advantageously configured in such a way that an almost diffraction-limited image quality for the relevant wavelengths of the imaging modality is achieved over the entire object field without significant vignetting.

Analogous to the first and second embodiment, the punctiform Raman excitation or detection can take place in a second beam path which comprises the second optical fiber 11, the beam shaping element 12, the deflector element 13, the filter 14 and the beam splitter filter 15. Correspondingly, Raman detection or Raman excitation is then realized in the first beam path comprising the filter 15, the lens elements 4, 5, 25, 26, the mirror scanner 10, the filter 16, the deflection element 18 and the beam-forming optical element 19 in the first optical fiber 9. In this case, the mirror scanner 10 is in the neutral rest position, so that the confocality between excitation and detection is given.

Figure 9:
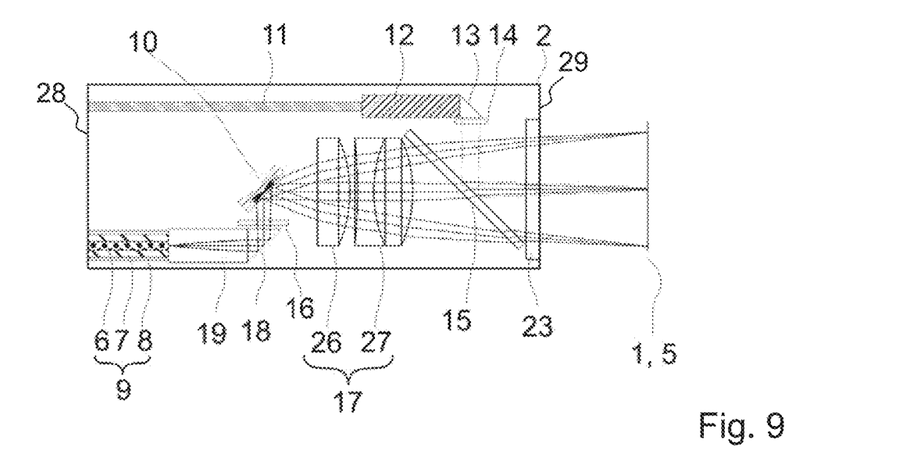

FIG. 9 shows another example of the optical probe 2. In this example, a miniaturized mirror scanner 10 with a comparatively large object field and a low numerical aperture between 0.05 and 0.12 is used for scanning, as is desirable for optical coherence tomography (OCT). Compared to the previous examples, an advantageously simplified optical system achieves a large depth of field of the image in the object 1 to be examined (e.g. tissue), and an almost diffraction-limited image quality can be achieved over the entire image field. The optical element 17 following the mirror scanner 10 consists of only one plano-convex lens 26 and one doublet lens 27. Due to the very weak divergence of the beam path, the intermediate image plane 5 can simultaneously function as an object plane. The lens elements 3, 4 used in the previous examples can be advantageously omitted. For protection, the probe 2 is preferably only terminated by a front window 23. Raman excitation and detection can be carried out analogously to the examples described above, whereby the beam shaping element 12 and the deflecting element 13 are configured advantageously in terms of divergence and spot size for optimum Raman light yield.

In order to make the probe 2 as compact as possible, it may be advantageous in the previously described examples of the optical probe 2 to implement the beam-shaping optical elements 12, 19 as GRIN lenses with flat end faces. Furthermore, it is advantageous to configure the deflection elements 13, 18 as prisms, whereby other deflection angles than the 90° angles shown can also be favorable in order to make the optical probe 2 as compact as possible. It can also be advantageous to configure the beam splitter filter 15 as a prism beam splitter cube, whereby deviations from the 90°/45° geometry can also be useful here in order to simplify the layer design of the beam splitter filter 15. In addition, the optical probe 2 can be simplified if the filters 14, 16 are applied to the surfaces of the lens elements 3, 4 or the deflection element 13, 18 as a coating.

The invention is not limited by the description given in the examples. Rather, the invention includes any new feature and any combination of features, which in particular includes any combination of features in the claims, even if that feature or combination itself is not explicitly stated in the claims or examples.

What is claimed:

1. An optical probe comprising:
   a rear end for connection to an evaluation unit and a front end for optically inspecting an object;
   a first optical beam path for a scanning imaging method and a second optical beam path for a spectroscopic method;
   a first optical fiber in the first optical beam path configured to guide an illumination light for the scanning imaging method toward the front end of the probe and to guide object light returning from the object to the rear end of the probe;
   a fiber or mirror scanner configured to laterally deflect the first optical fiber or the illumination light emerging from the first optical fiber for scanning the object in the scanning imaging method;
   a second optical fiber in the second optical beam path configured to guide an excitation light or a detected object light for the spectroscopic method; and
   a beam splitter filter, wherein the first optical beam path of the scanning imaging method and the second optical beam path of the spectroscopic method are partially brought to overlap by the beam splitter filter in the probe,
   wherein the probe has a diameter of not more than 5 mm.

2. The optical probe according to claim 1,
   comprising at least one lens element for beam shaping at least one of the illumination light and the object light, wherein the at least one lens element, is arranged at least regionally between the first optical fiber and the front end of the probe.

3. The optical probe according to claim 1,
   wherein the second optical fiber is configured to guide the excitation light of the spectroscopic method, and the first optical fiber is configured to guide the detected object light of the spectroscopic method, or
   wherein the first optical fiber is configured to guide the excitation light of the spectroscopic method and the second optical fiber is configured to guide the detected object light of the spectroscopic method.

4. The optical probe according to claim 1,
   wherein the beam splitter filter is wavelength-selective and is configured to separate the excitation light and the detected object light of the spectroscopic method from each other.

5. The optical probe according to claim 1,
   wherein the beam splitter filter is transmitting for the illumination light and for the object light returning from the object of the scanning imaging method.

6. The optical probe according to claim 1,
   wherein the first optical fiber comprises an inner fiber core and an outer fiber core, the outer fiber core having a core diameter between 20 µm and 300 µm and a numerical aperture between 0.11 and 0.4.

7. The optical probe according to claim 1,
   wherein the second optical fiber has a core diameter from 3 µm to 300 µm and a numerical aperture from 0.08 to 0.4.

8. The optical probe according to claim 1,
   wherein the probe comprises at least one lens element comprising at least one gradient index lens.

9. The optical probe according to claim 1,
   wherein the beam splitter filter merges the first optical beam path and the second optical beam path in a direction from the rear end to the front end or separates them from each other in an opposite direction.

10. The optical probe according to claim 1,
    wherein the second optical beam path comprises at least one optical filter for selecting a wavelength range for the spectroscopic method.

11. The optical probe according to claim 1,
    wherein the spectroscopic method is Raman spectroscopy.

12. A method for operating an optical probe according to claim 1,
    wherein the object is examined by the probe with at least one scanning imaging method and with at least one spectroscopic method.

13. The method according to claim 12,
    wherein the scanning imaging method comprises one of the following methods: optical coherence tomography (OCT), coherent Anti-Stokes Raman scattering (CARS) microscopy, stimulated Raman scattering (SRS) microscopy, multiphoton microscopy, second-harmonic generation (SHG) multiphoton microscopy, confocal single photon fluorescence, and reflection microscopy.

14. The method according to claim 12,
    wherein the spectroscopic method is Raman spectroscopy.

* * * * *